(12) United States Patent
Di Palma

(10) Patent No.: US 7,217,256 B2
(45) Date of Patent: May 15, 2007

(54) LOCKING CATHETER HUB

(75) Inventor: Giorgio Di Palma, Queensbury, NY (US)

(73) Assignee: AngioDynamics, Inc., Queensbury, NY (US)

( * ) Notice: Subject to any disclaimer, the term of this patent is extended or adjusted under 35 U.S.C. 154(b) by 127 days.

(21) Appl. No.: 10/821,472

(22) Filed: Apr. 8, 2004

(65) Prior Publication Data

US 2005/0107739 A1 May 19, 2005

Related U.S. Application Data

(60) Provisional application No. 60/520,606, filed on Nov. 17, 2003.

(51) Int. Cl.
*A61M 29/00* (2006.01)
(52) U.S. Cl. .................................. 604/104; 604/107
(58) Field of Classification Search ............. 604/95.04, 604/263, 523
See application file for complete search history.

(56) References Cited

U.S. PATENT DOCUMENTS

| 4,600,402 | A | 7/1986 | Rosenberg |
| 5,352,198 | A * | 10/1994 | Goldenberg et al. ..... 604/95.04 |
| 5,399,165 | A | 3/1995 | Paul, Jr. |
| 5,419,764 | A | 5/1995 | Roll |
| 5,514,112 | A | 5/1996 | Chu et al. |
| 5,522,400 | A | 6/1996 | Williams |
| 5,730,724 | A | 3/1998 | Plishka et al. |
| 6,042,577 | A * | 3/2000 | Chu et al. .................... 604/523 |
| 6,508,789 | B1 | 1/2003 | Sinnott et al. |
| 6,673,060 | B1 | 1/2004 | Flemming, III |
| 6,699,233 | B2 * | 3/2004 | Slanda et al. ............... 604/533 |
| 7,087,038 | B2 | 8/2006 | Lee |
| 2003/0181854 | A1 | 9/2003 | Sauvageau |
| 2004/0039339 | A1 | 2/2004 | Magnusson |

* cited by examiner

*Primary Examiner*—Catherine S. Williams
(74) *Attorney, Agent, or Firm*—Reed Smith LLP; Harry K. Ahn

(57) ABSTRACT

A catheter designed to be anchored in an internal cavity of a patient such as a drainage catheter employs a novel hub design. The hub has a slide member slidably coupled to the hub and a latch that latches the hub and the slide member together when the slide member slidably moves relative to the hub. Preferably, latching takes place when the slide member moves relative to the hub in an axial direction of the hub. A manually operable release member is provided on the hub such that the latch is disabled from unlatching unless the release member is manually operated. This feature advantageously limits a person's ability to accidentally unlatch the hub.

29 Claims, 10 Drawing Sheets

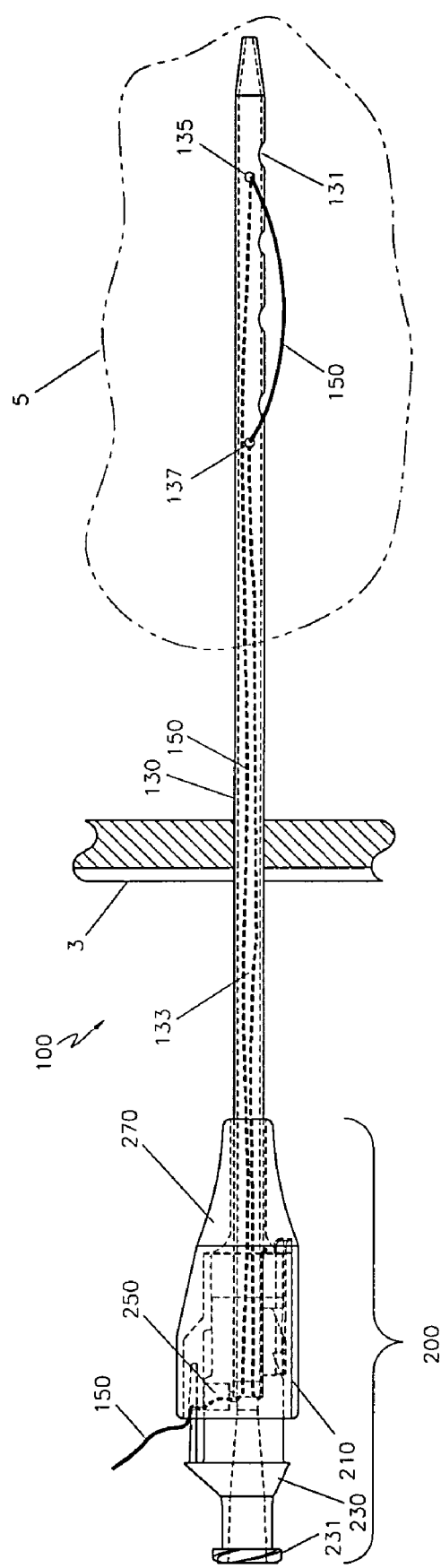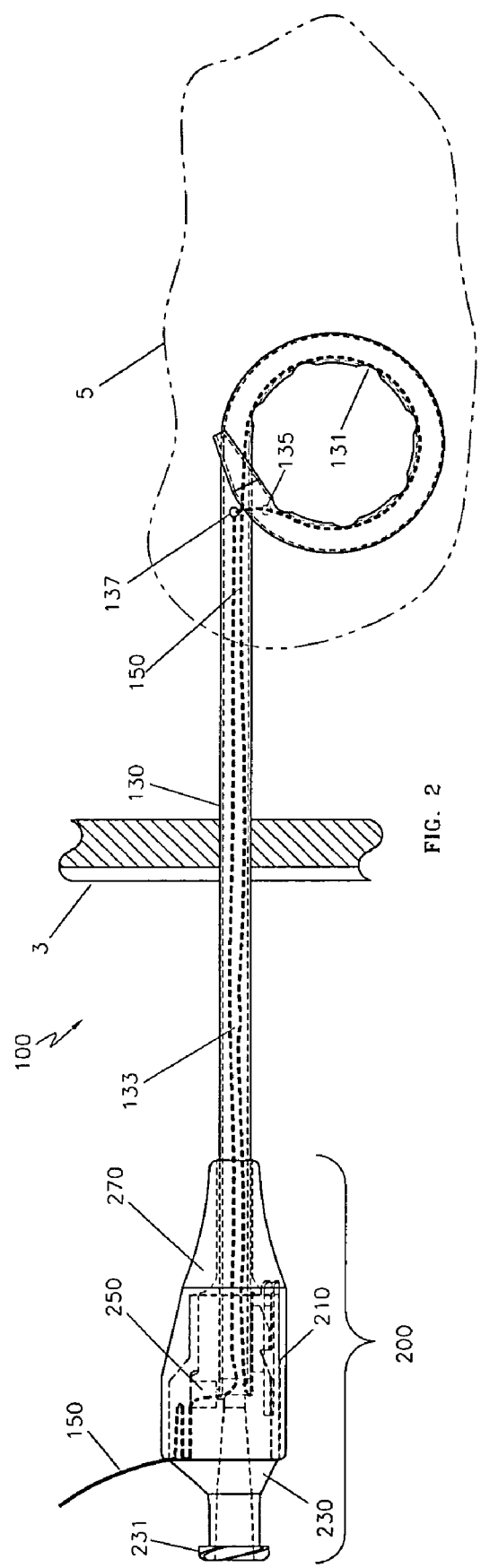

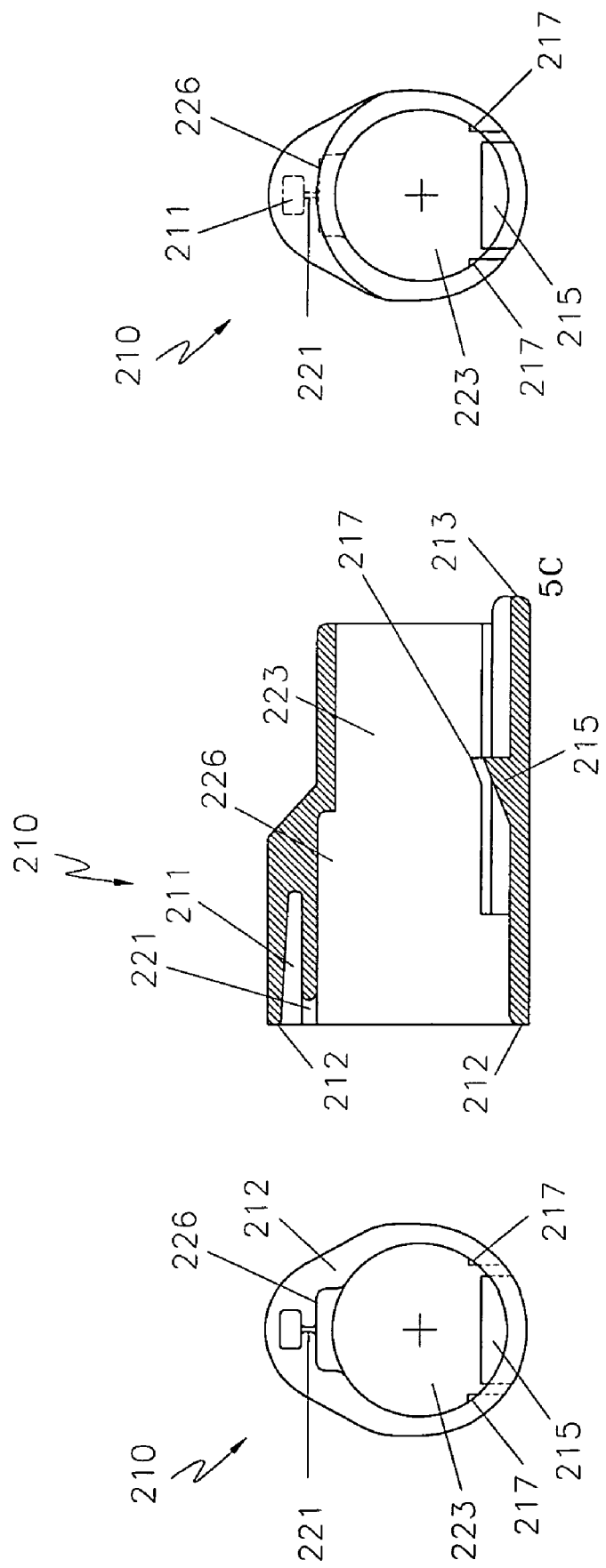

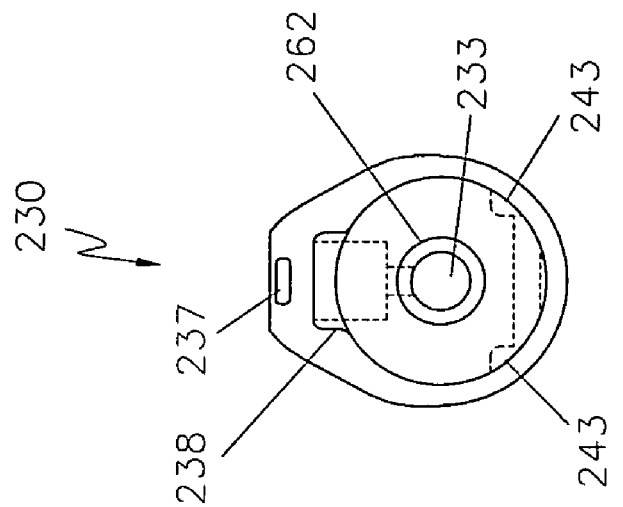
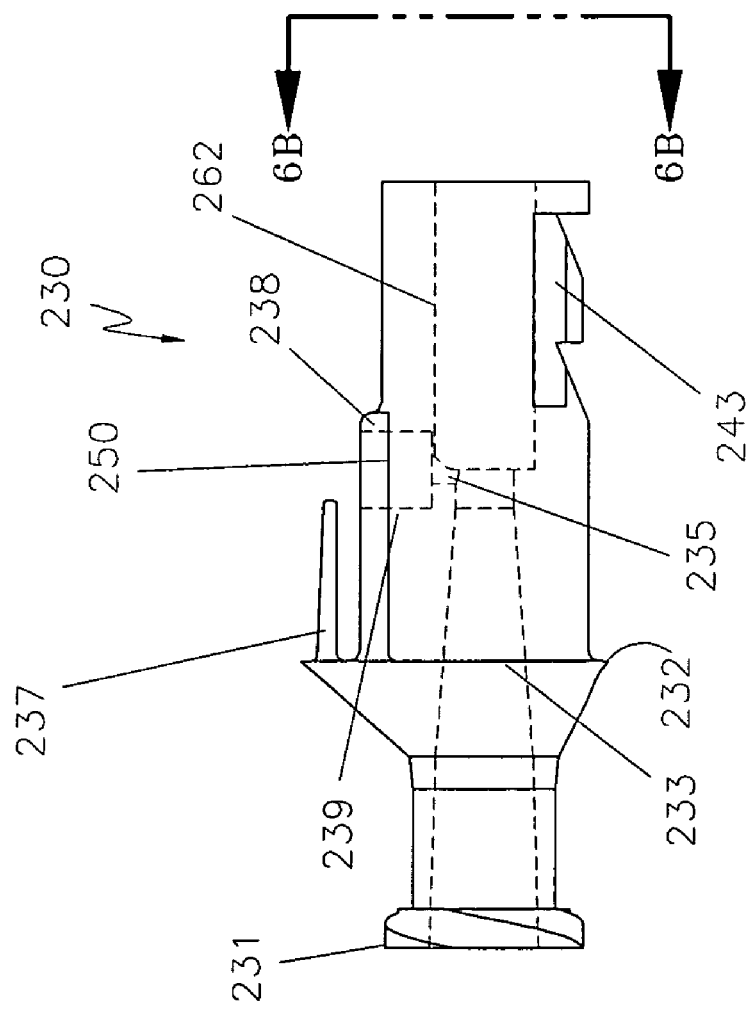
FIG. 6B
FIG. 6A

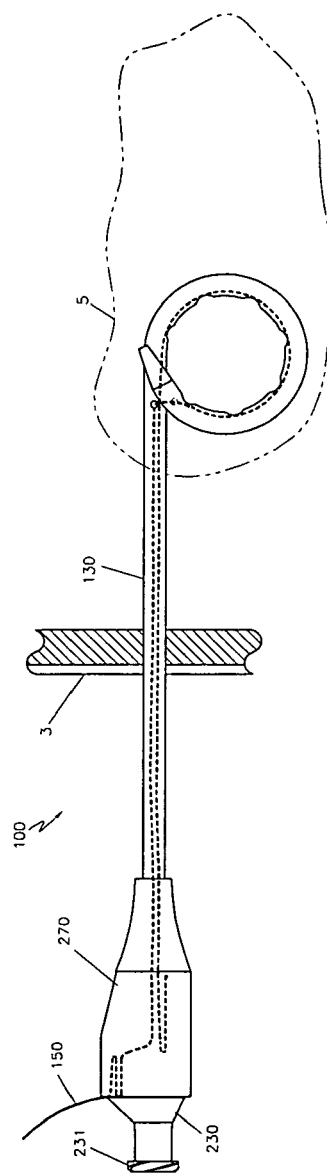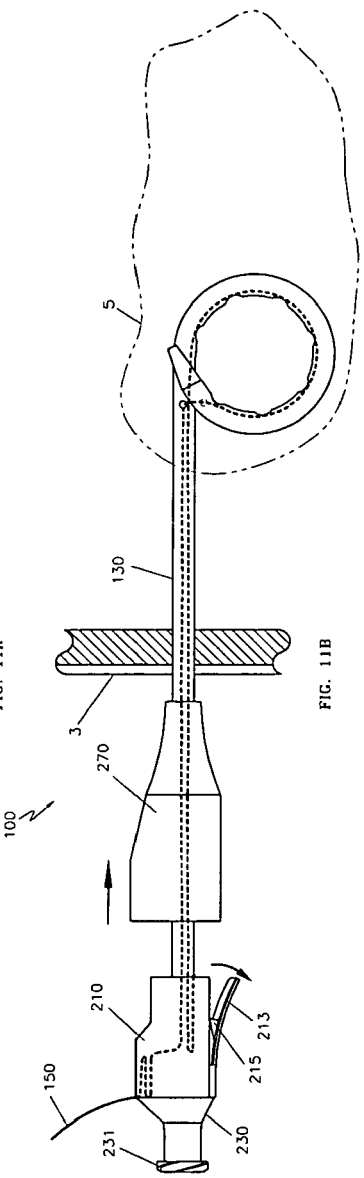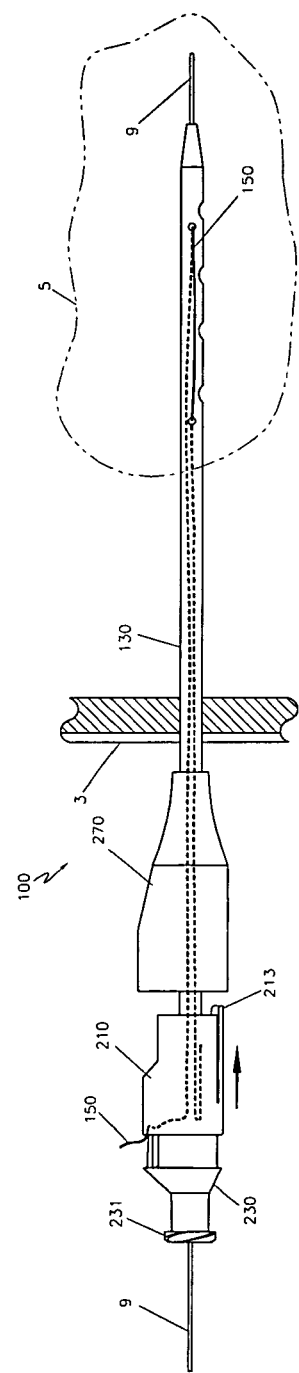

LOCKING CATHETER HUB

CROSS REFERENCE TO RELATED APPLICATION

This application claims priority to U.S. provisional patent application No. 60/520,606, filed Nov. 17, 2003, which is incorporated herein by reference.

FIELD OF THE INVENTION

The present invention relates to a catheter designed to be inserted into a body cavity, and more specifically, to a catheter having an anchoring end.

BACKGROUND OF THE INVENTION

There are several types of prior art catheters designed for insertion into a body cavity of a patient. These typically employ an anchoring device in the end of the catheter intended to reduce the risk of accidentally pulling the catheter out of the cavity. One type of such catheter employs a suture that is accessible from outside of the patient, passes through a connector on the catheter into internal opening (or lumen) of the shaft of the catheter. It then exits through the tip and reenters the lumen at a more proximal location where it can be secured inside of the lumen or on the connector. A medical professional inserting the catheter then pulls on the suture causing the distance between where the suture exits the catheter and where it reenters the catheter to be reduced. This effectively causes the distal section of the catheter to form an anchoring shape. The suture is then secured holding the distal end of the catheter in this anchoring shape. If the catheter is pulled, its distal end in the anchoring shape is pulled against the wall of the cavity, resisting the pulling force, thereby preventing the catheter from being pulled out of the patient.

The catheter may also be manufactured with a pre-formed curl at its distal end, to facilitating curling once in the body cavity. To insert this type of catheter, a stiffening rod is placed through the lumen of the catheter causing it to straighten out. The catheter and rod are then inserted into the body cavity. Once inserted, the stiffening rod is removed causing the shaft of the catheter to curl to its original pre-curved shape. The pre-curved shape interacts with the internal surface of the cavity to resist removal of the catheter once inside a body cavity.

Alternatively, a guide wire is inserted using accepted medical procedures into the body cavity. A dilator may be used to open the insertion site before sliding the catheter over the guide wire and into the body cavity.

A suture is used to hold the catheter in its position after the catheter returns to its original pre-formed shape. The suture also provides increased retention capabilities to the catheter.

Since these catheters are inserted into a patient who is typically under local anesthesia, the patient is awake and uncomfortable. The patient may also be moving or fidgeting during the procedure while the physician is trying to secure the suture. The physician also has to secure the suture when wearing protective gloves. In addition, the flow of bodily fluids typically infected and unpleasant may be flowing from the catheter.

If a physician improperly inserts, or improperly operates one of these devices, substantial complications may arise that are described in detail later. These catheters should be designed such that they are intuitive to operate requiring little or no instruction. Such a device would minimize risk of improper insertion, and the time spent in 'guesswork' during a procedure in which the physician 'learns' the device.

Several devices are currently in use to secure the suture after the catheter has been placed. One prior art design employs a catheter shaft connected to a stopcock at the proximal end. The stopcock has an internal barrel that rotates in a cylindrical housing. The barrel has a center hole passing through it that may be aligned with the lumen of the catheter by rotating the barrel using a key attached to the catheter by a string or suture. A suture passes from the distal end of the catheter, through the shaft of the lumen, through the center hole in the barrel, and out of a proximal end of the stopcock. As the stopcock barrel is rotated the center hole is no longer aligned with the catheter lumen and seals off the lumen. As the barrel rotates, it also pinches the suture between the sidewall of the barrel and the stopcock housing on both sides of the barrel. The pinching of the suture secures it in place.

That design has disadvantages of not being intuitive to operate, not being as comfortable as other designs, compromising the integrity of the suture, requiring a separate key, and not providing a tactile or audible signal that the catheter is in the locked position as discussed in detail below.

The stopcock housing is marked with a lock and unlock position. If in the locked position, a medical professional intending to drain fluids from inside of the patient may mistakenly rotate the barrel from lock to unlock. This action will also release the suture allowing the catheter to be pulled out of the patient. Therefore, it is not very intuitive to operate.

Since this design employs a stopcock and barrel, the size of the connector is larger than most other designs. The larger size coupled with the fact that it does not have a soft covering, causes considerable discomfort to the patient. The catheter may be implanted in awkward locations and remain in place for extended periods of time, causing additional discomfort to the patient.

When the stopcock barrel is turned to secure the suture between the center opening walls in the barrel and the stopcock body, the contact is localized to two small pinch points. These pinch points flatten the suture causing weakened points in the suture. These weakened points are more prone to breakage than undamaged portions of the suture. Once the suture breaks, the distal end of the catheter is no longer locked in place, increasing the risk of catheter dislodgement.

Another problem is that even though there is a visual indication that the catheter is in the locked position, there is no positive tactile or audible feedback, (such as a snap) to the physician indicating when the connector has been placed in the locked position. This is a useful feature that is lacking in this design.

Another prior art catheter device is a c-clip design that employs a hub with a circumferential inset, connected to the proximal end of a catheter. A suture runs from the distal end of the catheter, through the lumen of the catheter, to an exit point through the sidewall of the hub. To lock, the suture is wrapped around the circumferential inset. A c-clip is provided that is intended to fit around the periphery of the hub, and clipped into the inset over the suture, thereby securing the suture.

The c-clip design is difficult to operate, even under optimum conditions. The c-clip is small and difficult to align in the inset. It will not snap into place unless properly aligned.

In addition to being difficult to lock, it is fairly easy to unlock. A patient, without the aid of tools, can pop the c-clip out of the inset, thereby causing the catheter to become unlocked. Therefore, it is not very tamper-resistant.

This design also does not make use of a smooth protective covering, thereby having the additional disadvantage of being uncomfortable to the patient.

There is another design on the market that employs a simple side hole in a catheter hub connected to the proximal end of a catheter. A suture extends from the distal end of the catheter, through the lumen, and passes from the lumen to outside of the hub through the side hole. A conical flexible strain relief portion surrounding the catheter shaft is designed to be pulled up over the hub and side hole, both sealing the hole and securing the suture.

Even though this design is very intuitive to use, employs a soft protective cover to aid in patient comfort, it does not properly secure the suture in place. If a moderate amount of pulling force is exerted on the catheter, the suture will slip causing the catheter to become unanchored, and increase the risk that the catheter will move out of position or become dislodged. The catheter is difficult to lock since tension must be maintained on the suture during the locking procedure to keep it from unraveling.

Even if the suture does not slip on its own, a patient may easily unlock this design by simply pulling the strain relief portion off of the hub. Therefore, this design is not very tamper-resistant.

One additional problem is that, due to the nature of the design, when the strain relief is not placed over the hub, the side hole opening leaks fluids that are in the catheter lumen.

Like the stopcock design above, it provides visual indication that it has been placed in the locked position, however it lacks positive tactile or audible feedback to the physician indicating that it has been placed in the locked position.

U.S. Pat. No. 6,508,789 assigned to Merit Medical Systems, Inc. of South Jordan, Utah ('789 patent) describes another prior art drainage catheter having a pre-formed curl and a suture that pulls on the distal end of the drainage catheter as described above. The '789 patent further describes a 2-part (proximal and distal) hub that interacts with the suture to pull in the suture and lock the suture in place. A plurality of fingers on the proximal hub forces the suture into a corresponding plurality of channels of the distal hub that mate with the fingers. This effectively pulls in, and shortens the suture. A device according to the '789 patent functions to cause the distal end of the catheter to curl toward the proximal end that locks into position.

A drawback with that device is that it is only capable of pulling in a fixed length of suture into the hub, and cannot be adjusted to pull more, or less than this fixed length of suture into the hub, as needed.

A second disadvantage is that the use of the fingers in channels, as opposed to the medical professional manually pulling on the suture, causes a loss of tactile feedback. The medical professional uses tactile feedback to determine if the tip of the catheter is moving freely or if it is trapped, caught or tangled when anchoring the catheter.

A third disadvantage is that since there is no tactile feedback, if the device is trapped, caught or tangled, and the medical professional 'forces' the device to lock, the increased friction of the suture as it passes through each of the plurality of fingers and channels may cause breakage of the suture, making the device unusable.

The design in the '789 patent is also not very intuitive to operate. The physician pushes the proximal hub into the distal hub thereby pulling in a length of the suture into the hub. Therefore, it is not very intuitive to 'push' to 'pull' in the suture.

One additional drawback with that design is that there are a series of internal crevices within the fluid path that cannot be flushed and cleaned. As specified above, these types of catheters are typically used to remove infected bodily fluids. The fluids, if allowed to remain in the hub of the Sinnot design could cause considerable infection.

U.S. Pat. No. 5,399,165 assigned to Cook, Inc. ('165 patent) describes a drainage catheter employing a similar distal curl and suture arrangement. The '165 patent describes the use of a lever on the catheter hub that actuates a cam causing pressure to be placed on the suture, at a specific point, thereby locking the suture in place.

This design results in a large, bulky catheter connector that is uncomfortable for the patient. The design is also not very tamper resistant since the patient, without the use of tools, can flip the lever to unlock the suture, allowing the catheter to become unanchored, causing increased risk that the catheter will move out of position or become dislodged.

This design also suffers from the problem that there is an open hole to the inside of the lumen when it is in the unlocked position (when the lever is up), thereby allowing leakage.

One of the greatest shortcomings of this design is that it employs a single localized point of contact with the suture. Therefore, it does not positively secure the suture, and allows the suture to slip.

Moreover, the localized pressure on the suture where the cam presses against the suture, employed to secure the suture, causes a weakening of the suture at that point. If the suture breaks, there is the possibility that the catheter will reposition itself so that it does not function as well as intended, or potentially can become dislodged. This may require a medical procedure to be performed to insert a replacement catheter.

Therefore, there is a need for a catheter designed to be secured in a body cavity that: a) is simple to operate, b) is intuitive to operate without requiring much instruction, c) is comfortable to the patient, d) is small and not bulky, e) positively secures the suture, f) minimizes damage to the suture, g) provides audible, or tactile feedback when locked, h) is sufficiently tamper-resistant, i) can be completely flushed and cleaned, j) does not leak when in either the locked or unlocked positions, and k) does not loosen when attached to, or detached from other equipment.

SUMMARY OF THE DISCLOSURE

According to the principles of the present invention, a catheter device having an anchoring end is provided. The catheter device includes a hub which is attached to a proximal portion of a flexible shaft. A cord runs from a distal portion of the shaft through a lumen of the shaft and then exits from the hub at its free end. The hub has two members that are slidably movable relative to each other, and a latch that latches the two members together. The hub has an unlatched state that allows pulling of the cord such that the distal portion of the shaft forms an anchoring shape, and a latched state in which the latch latches the first and second members together when one hub member slidably moves relative to the other member so as to secure the cord to the hub.

Preferably, the latch latches the two hub members together with a sliding motion of one hub member relative to the other hub member in an axial direction of the hub.

In another aspect, a manually operable release member is provided on the hub such that the latch is disabled from latching unless the release member is manually operated. According to the invention, this features provides asymmetry in the latching and unlatching operation. For example, latching can be accomplished by pulling a second hub member towards a first hub member. Unlatching, however, cannot be accomplished by a simple reverse action of pushing the second hub member away from the first hub member. For unlatching, the release member is manually operated first before the second member can be pushed away from the first hub member. As can be appreciated by persons of ordinary skill in the art, this asymmetric feature advantageously limits a person's ability to accidentally unlatch the hub.

In another aspect, a strain relief is provided to at least partially cover the release member to further limit the ability of the person to unlatch the hub by forcing that person to expose the covered release member prior to unlatching.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 1 is an elevational view of a catheter system consistent with the present invention, with a hub in an unlatched position, prior to formation of the anchoring shape.

FIG. 2 is an elevational view of the catheter as shown FIG. 1, now in a latched position where the distal end of the catheter has been curled and the cord has been secured in place.

FIG. 5A is a sectioned view through the center of the slide of the latching hub assembly of FIG. 3.

FIG. 5B is an end-on view of the slide of the latching hub assembly of FIG. 3 viewed from the proximal end.

FIG. 5C is an end-on view of the slide of the catheter of FIG. 3 viewed from the distal end.

FIG. 6A is an elevational, view of the hub of the catheter shown in FIG. 3.

FIG. 6B is a cross-sectional view of the hub of FIG. 6A along lines 6B—6B.

FIG. 11A is an elevational view of the catheter of FIG. 1 in its latched position, illustrating how the catheter appears prior to removal.

FIG. 11B is an elevational view of the catheter of FIG. 1 illustrating how the latching hub assembly is unlatched to release the cord.

FIG. 11C is an elevational view of the catheter of FIG. 1 in its full unlatched and straightened position allowing the cord to move freely through the latching hub assembly.

DETAILED DESCRIPTION OF THE PREFERRED EMBODIMENTS

Figure 3:
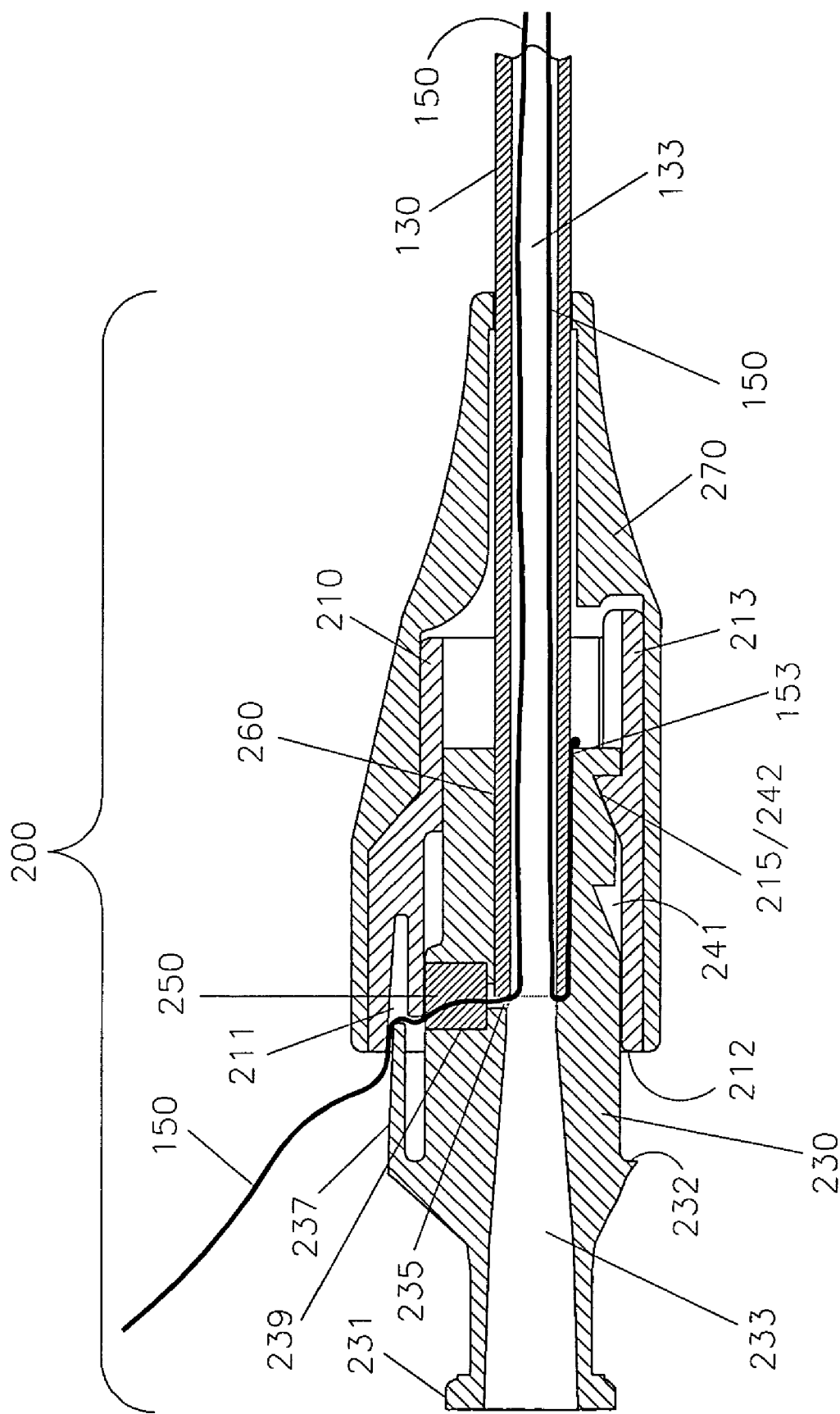
FIG. 3 is an enlarged sectioned view of a latching hub assembly of the catheter of FIG. 1 in the unlatched position.

A catheter 100 consistent with the present invention is shown inserted through the body wall 3 of a patient and then into a body cavity 5. The catheter may be for the purposes of drainage of infected fluids, removal of urine, infusion of nutrition, or other uses.

FIG. 1 illustrates a catheter 100 having a locking or latching hub assembly 200 consistent with the present invention. Catheter 100 is comprised of a catheter shaft or tube 130 having a proximal and distal portion or end. The distal end typically has at least one hole 131 and another hole 137 into at least one internal lumen 133. Even though the catheter shown in the figures has only a single lumen, any number of lumens may be used with the present invention.

The proximal end of the catheter shaft is connected to a hub 230 of a latching hub assembly 200 at hub/shaft bond 260, shown in FIG. 3. The shaft 130 is secured to the hub at bond 260 using adhesive or other bonding techniques well known in the art. One end of a cord 150 such as a suture is permanently attached to the hub 230 within bond 260 at location 153. Optionally, the permanently secured end of the suture 150 may include a knot for added reinforcement.

Latching hub assembly 200 is shown here in its "unlatched" position, in FIG. 1 where a slide member 210 is spaced away from and slidably coupled to the hub member 230. Suture 150 is free to move into or out of latching hub assembly 200. During the insertion procedure, catheter shaft 130 is substantially straight prior to being retracted by suture 150.

Shaft 130 may be a straight flexible shaft, or alternatively can be a shaft having a distal end with any number of pre-formed, anchoring shapes, such as a curl, accordion, or other shape typically known to anchor catheters within a body cavity. This preformed shape would facilitate anchoring of the distal end of the shaft 130 when suture 150 is retracted.

In the embodiment shown in FIGS. 1 and 2, a suture 150 is anchored at the location where shaft 130 is connected to hub 230. The cord 150 then runs at least about a portion of the length through lumen 133, exits at or near the distal tip of shaft 130 at distal suture hole 135, and reenters shaft lumen 133 at proximal suture hole 137. The cord 150 then passes back through the length of lumen 133 through a seal 250 of hub 230 and out of latching hub assembly 200 where it is accessible to the physician.

In another arrangement, suture 150 may exit from the proximal suture hole 137 on shaft 130, and reenter lumen 133 at distal suture hole 135 near the distal tip of the catheter.

In still another arrangement, suture 150 may be attached near the tip, enter lumen 133 at a more proximal location, run through lumen 133, through seal 250 of latching hub assembly hub 230 and outside of latching hub assembly 200 to leave a free end which is accessible to the physician.

In order to reduce the risk that these catheters are pulled out after insertion, the distal end is pulled back into an anchoring position. When a pulling force is applied to the proximal end of the catheter, the curled end is forced against the internal cavity wall 7, preventing its removal from the body cavity 5.

As shown in FIG. 2, after the suture 150 is pulled back, the distal end of the shaft 130 becomes curled, or if pre-formed, the distal end curls by itself into a pigtail anchoring shape and the suture holds the end in its anchoring shape.

Typically, luer connector 231 attaches to additional medical apparatus such as suction, or fluid collections. Connector 231 is attached by rotating corresponding mating connector components together. They are typically disconnected by the same method in a reverse direction of rotation. This has been an issue in some prior art devices since the suture is released by rotating a component near the connector. Sometimes when disconnecting the connector components, the suture would be inadvertently released, causing the device to no longer be anchored, and to move out of its intended position.

As shown in FIGS. 1 and 2, latching hub assembly 200 for securing a suture, is comprised of hub portion 230, a slide portion 210, interacting together to secure suture 150. Suture 150 passes from inside latching hub assembly 200 through seal 250 and out of latching hub assembly 200. In its unlatched position, suture 150 passes freely through latching hub assembly 200.

However, when the connector is in a latched position as shown in FIG. 2, suture 150 is trapped between the slide 210 and hub 230 thereby securing suture 150 in the desired position.

Figure 4:
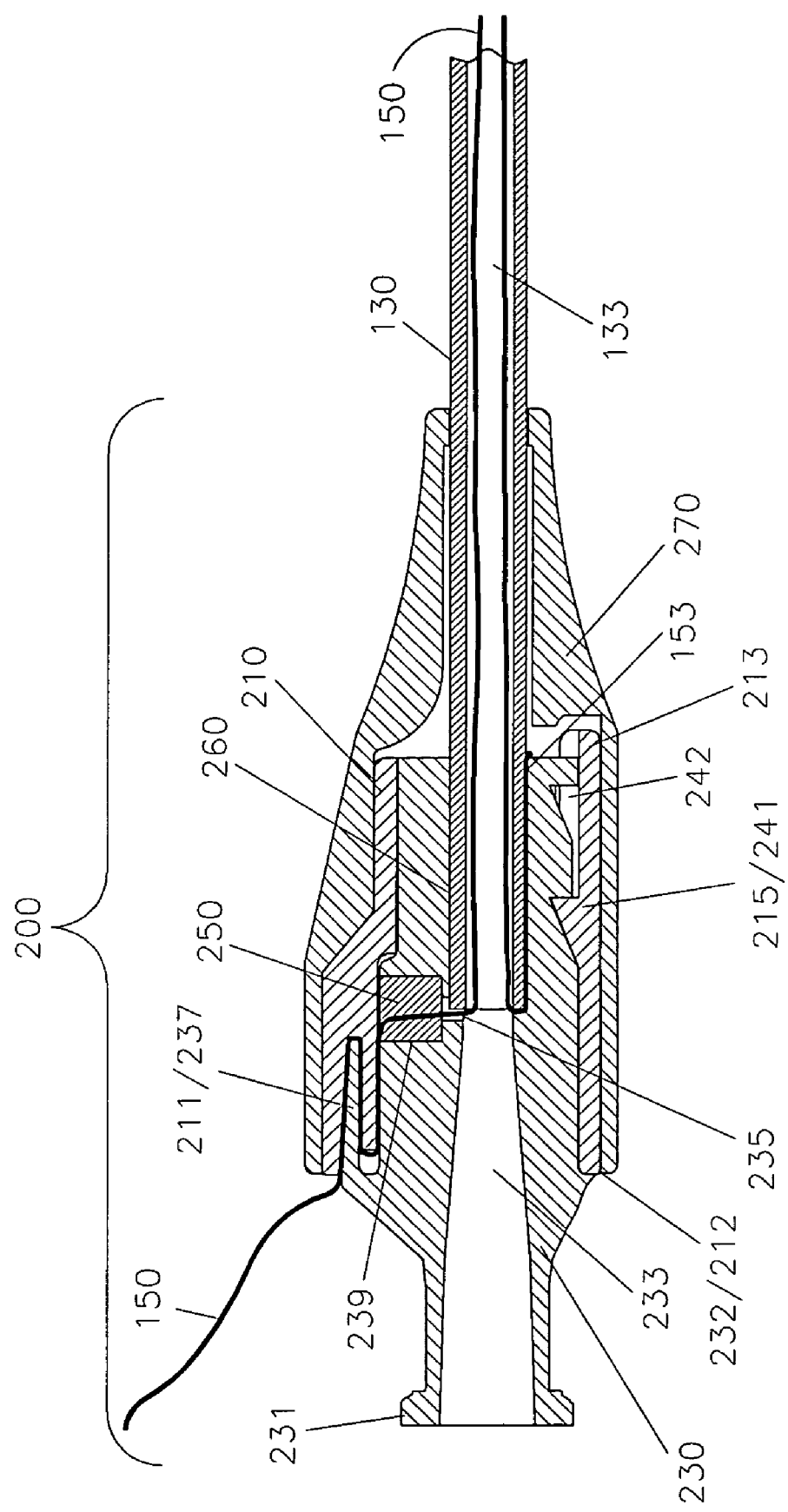
FIG. 4 is an enlarged sectioned view of the latching hub assembly of the catheter of FIG. 2 in the latched position.

FIGS. 3 and 4 show an enlarged cross sectional view through the center of latching hub assembly 200 in greater detail in the unlatched and latched positions, respectively.

The latching hub assembly 200 is shown in a full unlatched position in FIG. 3. Slide 210 slidably attaches to hub 230. Hub 230 has luer connector 231 for connection to other medical equipment. Hub 230 has a through lumen 233 that passes through the length of hub 230 allowing fluids to be passed through it to equipment connected to luer connector 231. Suture 150 is shown passing into a slide recess 211 of slide 210, and around a tongue 237 of hub 230. Suture 150 then passes through a seal 250, through suture channel 235 and into through lumen 233.

In the full-unlatched position, a projection such as a lock catch 215 as shown in FIG. 3 is seated or received in a second full open recess 242 to prevent the slide member 210 from sliding off the hub member 230. As slide 210 moves axially toward hub 230, lock catch 215 moves out of full open recess 242 and slides along surface of hub 230.

Also, in its full unlatched position, suture 150 is free to be pulled in or out of latching assembly 200, curling the distal tip of the catheter. The tension exerted provides direct tactile feedback of the motion of the tip to the physician.

Hub 230 is designed to mate with slide 210 such that a mating surface (212 of FIGS. 5A, 5B) of the slide 210 butts up against flange 232 as shown in FIG. 4. In the most basic preferable form of the present invention, hub 230 fits tightly into slide 210 when pushed together and are held together by a friction fit.

Slide 210 moves along hub 230 to the point where lock catch 215 fits into closed lock recess 241, thereby snapping into place and placing the connector in the "latched" position. In the latched position, suture 150 is no longer free to move and is "latched" in its current position. In its latched position, lock catch 215 snaps into lock recess 241 (shown in FIG. 3), and flange 232 abuts the mating face 212. In the embodiment shown in FIG. 3, the lock catch 215 and the lock recess 241 define a latch. Also in this embodiment, suture 150 is shown secured between the interacting surfaces of tongue 237 and slide recess 211.

FIGS. 5A, 5B and 5C show an embodiment of the slide 210 of the present invention. FIG. 5A is an elevational view showing a section through the center of slide 210. FIG. 5B is a view of slide 210 from the proximal end. FIG. 5C is a view of the slide from the distal end. Slide 210 will be described in connection with hub 230 of FIGS. 6A and 6B. FIG. 6A shows an elevation view of hub 230 from the side. FIG. 6B shows the same hub as viewed from its distal end.

Opening 223 of slide 210 is sized to fit around the surface of hub 230. Slide recess 211 is shaped and positioned to receive hub tongue 237. As stated earlier, slide 210 may optionally include a lock catch 215 that corresponds to, and latches into the hub lock recess (241 of FIG. 3) when slide 210 and hub 230 are fully pushed together in a latched position.

A release member such as a release tab 213 carrying lock catch 215 is connected to slide 210 at its distal end. It is preferred that release tab 213 extend slightly past the end of slide 210, allowing access to the tab.

In order to allow slide 210 to freely slide forward and backward on hub 230, without allowing slide 210 to slide off of hub 230, at least one slot 243 is employed on the hub 230 (FIG. 6). A slide protrusion 217 rides in slot 243 to the end of slot where it stops slide 210 from sliding off of hub 230. In an optional embodiment, inner surface of slide 210 may be angled inward moving from proximal to distal end of slide 210, such that as slide 210 moves onto hub 230, it presses downward against seal 250.

The latching hub assembly 200 is designed to prevent axial rotation of the slide 210 around the hub 230 relative to the hub lumen 233. Hub 230 includes an anti-rotation slide protrusion such as a key 238, shown in FIG. 6. Anti-rotation key 238 slideably fits and sized to be received within an anti-rotation longitudinal slot such as a key recess 226 of slide 210, shown in FIG. 5A through 5C. Key 238 and recess 226 prevent axial rotation of the slide 210 in both the unlatched and latched position of latching hub assembly 200. This anti-rotational feature limits twisting of the slide 210 relative to hub 230 when syringes or other medical accessories are connected or disconnected to the luer connector 231 of the hub 230. The expanded diameter of the hub 230 at anti-rotation key 238 also provides added depth to seal recess 239, allowing for a thicker seal 250.

Hub 230 includes a suture groove 221, illustrated in FIGS. 5A through 5C. Suture groove 221 provides a vertical channel for suture 150 in both the latched and unlatched positions of latching hub assembly 200. Providing a non-tension pathway through the suture groove 221 ensures that the suture 150 is not pinched, squeezed or otherwise damaged by the proximal end of the hub tongue 237. The groove 221 also ensures proper alignment of the suture between slide recess 211 and hub tongue 237.

Figure 7A:
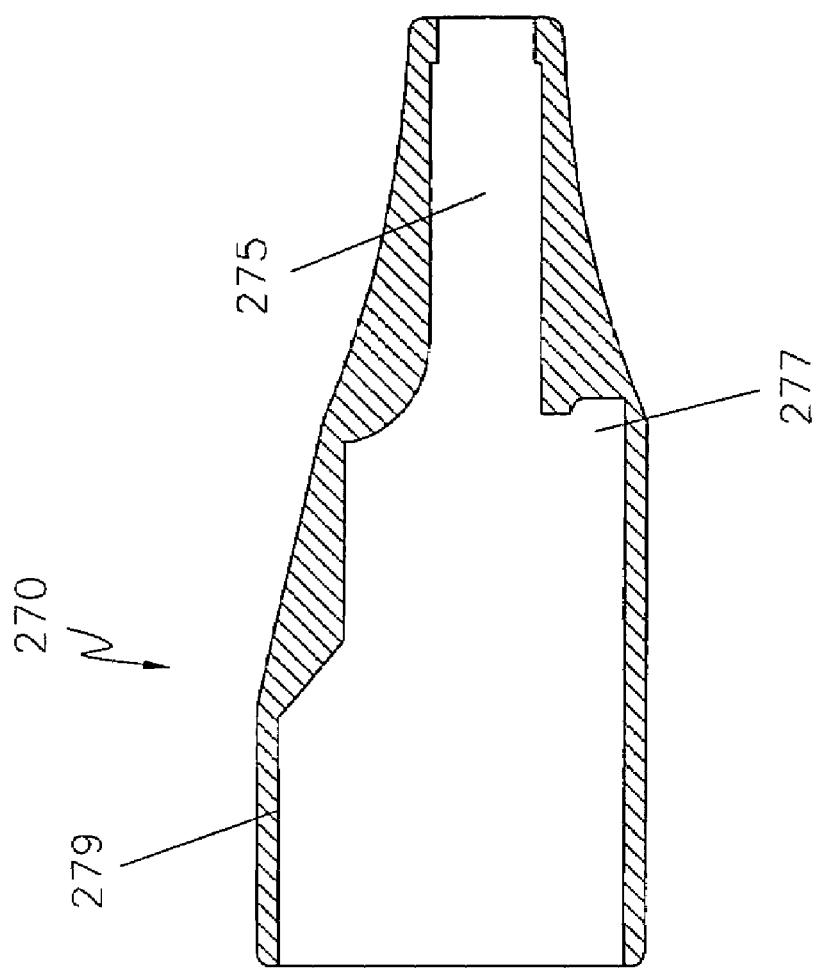
FIG. 7A is an elevational, sectioned view through the center of the strain relief unit of the catheter shown in FIG. 3.
Figure 7B:
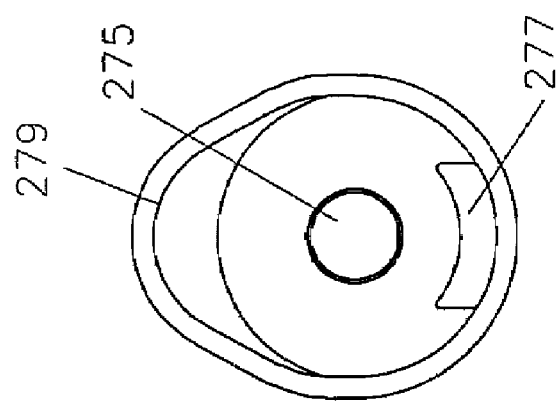
FIG. 7B is an end-on view of the strain relief unit of the catheter of FIG. 3 as viewed from its distal end.

A strain relief unit 270 as shown in an elevational sectioned view in FIG. 7A and as it appears as viewed from the proximal end in FIG. 7B performs several functions such as: a) making the device more comfortable for the patient, b) minimizing kinking of catheter shaft 130, c) making the device more tamper proof, d) facilitating latching of the device, e) providing audible/tactile indication of latching. These features will be described in also referencing other figures of this application.

Strain relief 270 is preferably constructed of a soft, non-irritating material that minimizes discomfort when placed against the patient's skin for extended periods of time. Strain relief 270 smooth surface, covers sharp edges or corners of the latching hub assembly providing a smooth, continuous surface. This design is more comfortable than most competing prior art designs.

Strain relief unit 270 also has a distal end that extends from slide 210 over the junction of shaft 130 and hub 230 (FIGS. 3 and 4). Preferably it has a distal conical shape as shown in FIG. 7A. A through hole 275 of strain relief 270 is sized to surround and be slidably coupled with the catheter shaft 130 (FIGS. 1–4). It should be sized to prevent debris from collecting under it, however must be loose enough to allow strain relief 270 to slide down onto shaft 130. When strain relief 270 is positioned on slide 210, and shaft 130 fits through the through hole 275, the strain relief will resist any bending at the junction of the shaft 130 and hub 230. The strain relief 270 reinforces the shaft at the hub 230 area, thereby preventing kinking of the shaft.

FIG. 7A shows a sectioned view through the center of strain relief 270. In a preferred embodiment of strain relief 270, it fits over and covers all, or substantially all of slide 210. As it does, it is intended to at least partially cover slide release tab 213. In the embodiment shown in FIG. 7A, the portion of release tab 213 that extends out from slide 210 (FIGS. 5A, 5B, 5C), is received by a release tab cavity 277 of the strain relief 270.

When strain relief 270 is pushed over slide 210, release tab 213, fits into release tab cavity 277, covering release tab 213 which is used to unlatch the latching hub assembly 200. Strain relief 270 covers and restricts patient access to the release tab. Since the patient typically is not familiar with the functioning of the latching hub assembly, there is no visual cue of how to unlatch the device.

The inner surface 279 of strain relief 270 is sized to tightly surround slide 210, fitting snugly against release tab 213. Therefore, if a patient could gain access to a portion of release tab 213, the patient could not pull release tab 213 away from hub 230, since it is tightly held in place by inner surface 279 of strain relief 270. Therefore, due to both of these features, the device is substantially more tamper resistant.

Since strain relief 270 covers most of the device, it is not obvious from viewing the device how to unlatch it. A trained individual, such as the physician, who has been instructed in the operation of this invention, will, however, know how to unlatch the device.

The device is unlatched by first removing strain relief 270 from slide 210 thereby exposing the release tab 213. The physician then pulls release tab 213 away from the center of the catheter, causing latching hub assembly 200 to be released from its latched position. The physician may then reposition or remove the catheter. If repositioned, latching hub assembly 200 may again be placed in its latched position, and the strain relief 270 pushed over slide 210, covering it again.

As stated above, internal surface 279 provides a significant force resisting outward radial motion of release tab 213, thereby biasing the tab 213 toward the center of hub 230 (FIGS. 3 and 4). Since lock catch 215 rides on release tab 213, if lock catch is not in either full open recess 242, or lock recess 241, lock catch 215 slides along the surface of hub 230 holding release tab 213 in a direction away from the center of hub 230. Therefore, since it is biased inwardly by strain relief 270, when lock catch 215 come into contact with either lock recess 241, or full open recess 242, lock catch 215 is forced into, and held in either recess. This facilitates latching, or unlatching of the device.

As stated above, when the lock catch 215 is forced into lock recess 241 or full open recess 242, there is an audible snap and a corresponding tactile sensation of the tab snapping into place. This provides a definitive indication that the latching hub assembly is in its full open or latched position to the physician.

A seal (port) 250 holding a sealing material 253 is used to prevent leaking around suture 150 as shown in FIGS. 3 and 4. A conventional seal fitted into seal recess 239, such as one made of natural rubber, having a hole passing through it for suture 150 may be used.

Figure 8:
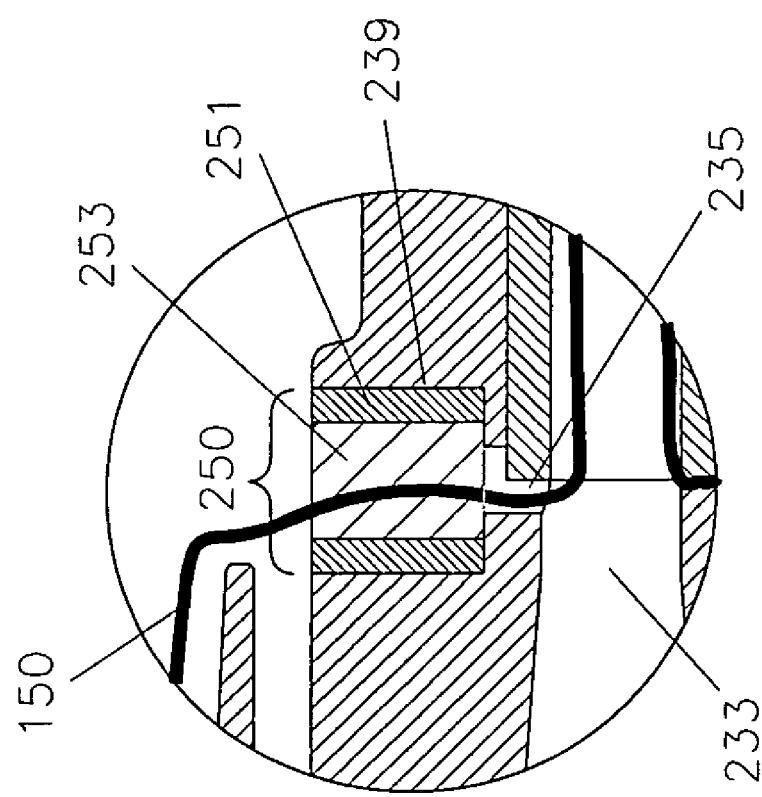
FIG. 8 is an enlarged sectioned view of an alternate embodiment of a seal consistent with the present invention.

Optionally, as shown in FIG. 8, the port/seal 250 may include a container 251 fitted inside of recess 239 that is filled with a deformable material 253. This material may be a semi-liquid material, such as silicone, that actively deforms. Suture 150 passes through the semi liquid material and into the lumen 233.

Figure 9:
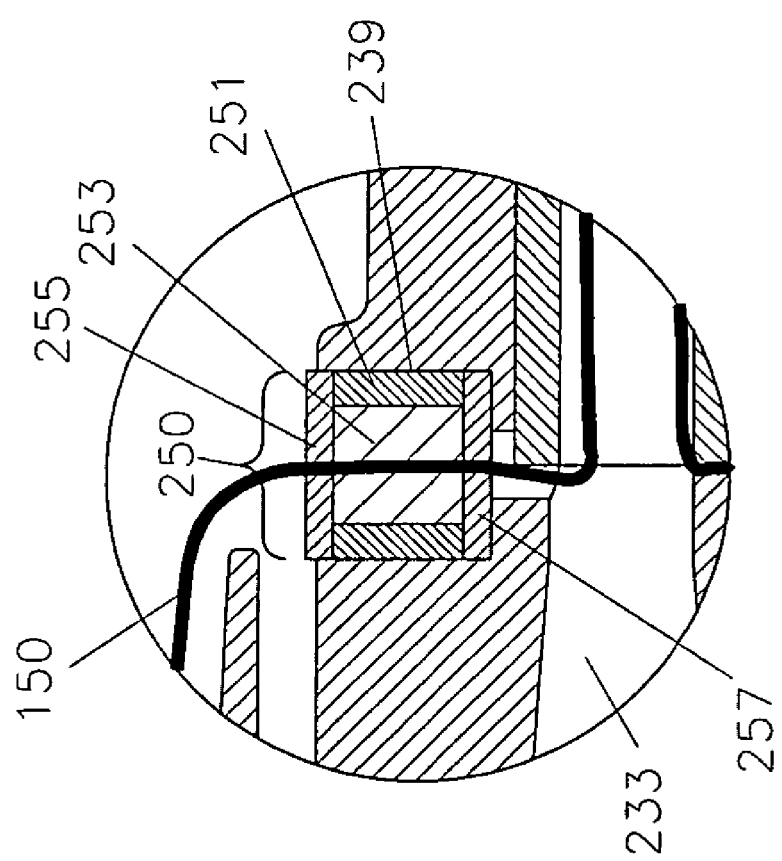
FIG. 9 is an enlarged sectioned view of another alternate embodiment of a seal consistent with the present invention.

In still another alternate embodiment of the present invention, as shown in FIG. 9, the port/seal 250 may further employ a top enclosure and a bottom enclosure 255 and 257, respectively. These enclosures employ a higher durometer material such as those intended for providing seals in other medical devices. One such acceptable material would be natural rubber. Both top and bottom enclosures 255 and 257 will have a hole for suture 150. When the suture 150 is pulled, the holes in the top and bottom seals may elongate providing spaces between the suture and the holes. The deformable material 253 deforms into the spaces thereby maintaining a tight seal.

A preferred method of using the catheter system 100 of the current invention will now be described with reference to FIG. 10 and FIG. 11. The procedure begins with the placement of the catheter system 100 in the body cavity 5. Typically ultrasound, computer tomography (CT), or fluoroscopy is used is to non-invasively locate the fluid pocket or other cavity 5. After the patient has been positioned and local anesthetic has been administered to the skin entry site, the catheter 100 is inserted into the cavity 5. Catheter 100 is placed using either the direct trocar technique or over a guidewire. With the direct trocar technique, catheter system 100 is assembled with an internal cannula/stylet (not shown). When fully assembled with the cannula/stylet, the catheter shaft 130 is straightened and stylet tip extends beyond the distal tip of catheter 100. The entire assembly is then inserted through the body wall 3 into the body cavity 5, after which the cannula/stylet assembly is removed from the catheter system 100.

Alternatively, the catheter system 100 may be inserted into the cavity 5 using a guidewire (not shown). Standard Seldinger access techniques, well known in the art, may be used to create an access track through which a guidewire is inserted. The catheter system 100 is then backloaded over the guidewire and advanced into the body cavity 5. The guidewire technique is often used for exchanging catheters using an existing access track.

Figure 10A:
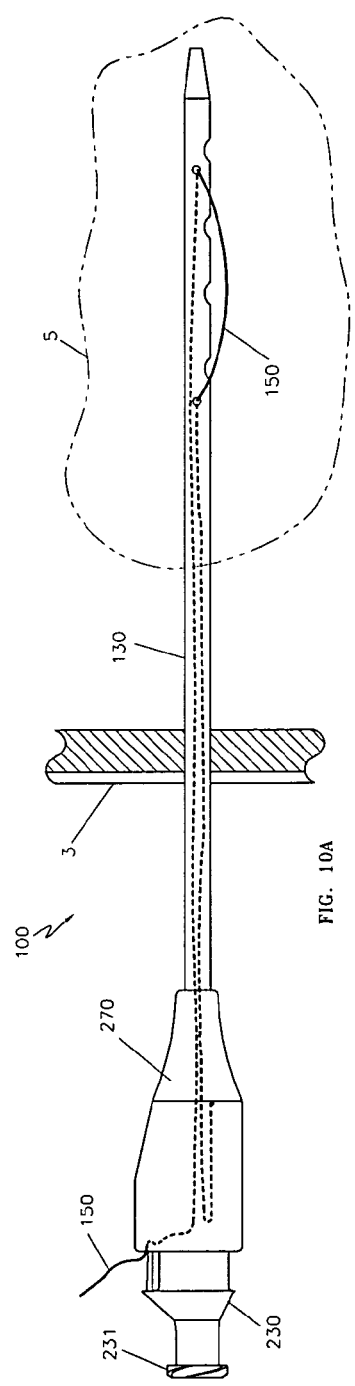
FIG. 10A is an elevational view of the catheter of FIG. 1 in its unlatched position, illustrating its insertion into a patient.

The catheter system of the current invention may be inserted using either of the access techniques described above. During the insertion, the latching hub assembly 200 is in the unlatched position as shown in FIG. 10A. Preferably, the catheter system 100 is packaged in the unlatched position so that no adjustment of the fitting is required by the physician prior to or during insertion. In the unlatched position, the strain relief 270 and slide mechanism 210 are positioned over the hub 230 such that the suture 150 is loose.

Figure 10B:
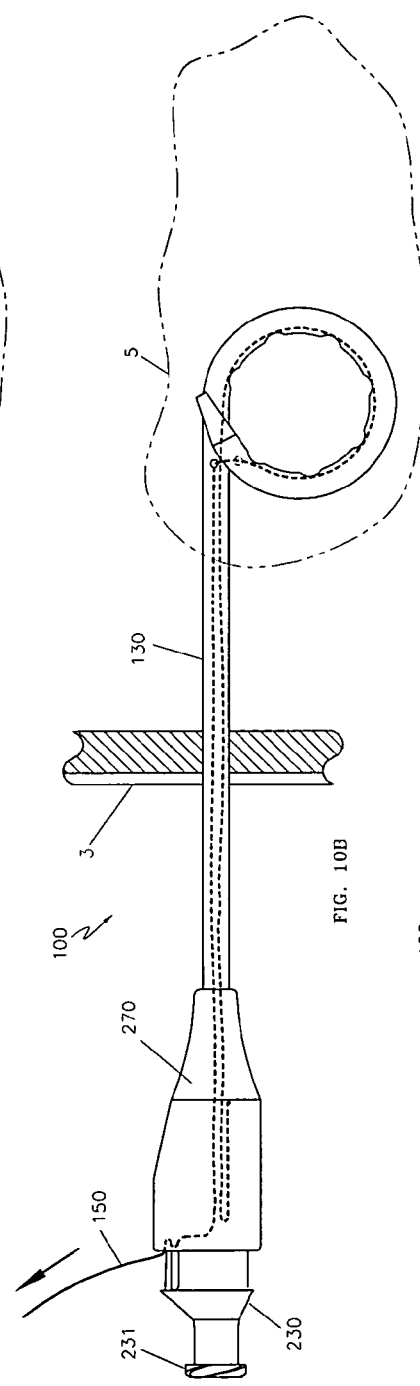
FIG. 10B is an elevational view of the catheter of FIG. 1 in its unlatched position, illustrating curling of the distal tip of the catheter by pulling on the cord, prior to latching the cord in place.

To form the anchoring shape at the distal end of the catheter 100, the physician pulls on the exposed suture 150 in a direction depicted by the arrow shown in FIG. 10B. This action causes the slack suture 150 at the distal end of the catheter shaft 130 to be tightened resulting in the formation of the anchoring shape, as is well known in the art.

Figure 10C:
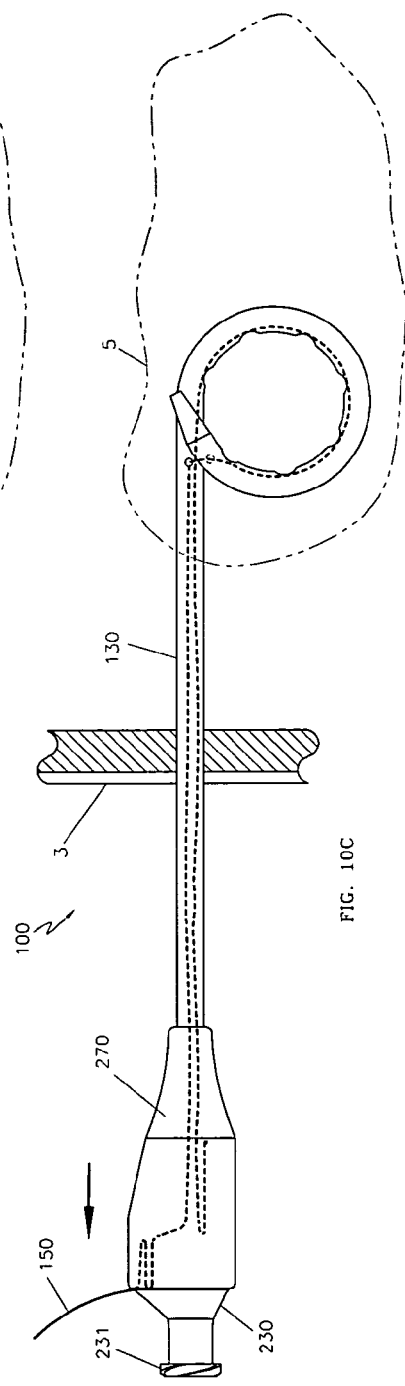
FIG. 10C is an elevational view of the catheter of FIG. 1 showing the latching hub assembly as it moves into its latched position, securing the cord.

To activate the latching mechanism, as shown in FIG. 10C, the physician simply moves the strain relief 270 proximally along the catheter shaft 130 until proximal face of the strain relief 270 is flush with the flange 232, as shown in FIG. 4. This action causes the slide 210 (not shown) to move proximally until it is in the latched position, with the suture positioned and trapped between the hub tongue 237 of the hub 230 and the slide recess 211. The design of the slide 210 and the hub 230 provide a tactile acknowledgment when the assembly is moved into the latched position. The physician will hear a snapping sound as the slide moves into place around the hub 230, causing the lock catch 215 to snap into lock recess 241 on the hub 230.

There are several advantages of the insertion method described above over prior art insertion methods. The activation of the latching mechanism is simple and intuitively obvious to the physician. By simply moving the strain relief 270 into position over the hub 230, the physician activates the latching mechanism. The design of the current invention does not require wrapping, activating the latch using a key or otherwise securing the suture relative to the hub, as is required in several prior art designs. A tactile acknowledgment provides the user with a simple way to confirm that the latching feature is activated. Providing a fitting assembly that is easily latched with a single movement combined with a tactile acknowledgement of the latch eliminates the complexities of current catheter latching mechanisms and provides a latching design that is intuitively obvious to the user.

As part of the placement procedure, the physician may flush the body cavity with saline or other procedural fluids. A syringe or other fluid delivery device is connected to the luer connector 231 of the catheter and fluids are administered through the hub lumen 233 and catheter shaft lumen exiting through the distal end of the catheter.

Alternatively, the physician may connect a syringe to aspirate the bodily fluids through the catheter. This step is often done to confirm that the device is positioned within the fluid pocket. Unlike some prior art design, the device of the current invention allows fluids to be injected and aspirated through the catheter when the catheter is in either the latched or unlatched position. Other catheters have been shown to leak fluids or air at the hub area when the catheter is in the unlatched position. The design of latching hub assembly 200, shown in the unlatched position in FIG. 3, will not leak fluids or air during injection or aspiration when unlatched because the suture path through the latching hub assembly 200 is effectively sealed by the seal 250.

When latched, the strain relief 270 provides a comfortable and protective barrier between the patient's skin surface 3 and the hub 230/slide 210 components. The overall size of the fitting assembly compared with other similar devices is small, minimizing patient discomfort from the external portion of the device contacting the skin surface. The strain relief, with its soft, compliant material, and smooth profile reduces patient discomfort while simultaneously providing protection against accidental unlatching by the patient or other health care provider. Although the latching mechanism can be deactivated by moving the strain relief 270 distally and releasing the tab 213, the slide 210 is completely covered by the strain relief 270 and accordingly is more resistant to accidental unlatching or patient tampering.

Catheters for the removal of bodily fluids may remain in place for an extended period of time. As such, the catheters should not only be resistant to accidental unlatching by a patient, but also to unlatching or loosing of the suture retention mechanism over time. The device and method of the current invention provides for a positive securement of the anchoring mechanism over extended periods of time. The suture path through the latching hub assembly 200 (shown in FIG. 4) provides an increased suture surface retention area over other devices. Specifically, the length of suture that is actively trapped and retained within the latching mechanism extends from the point at which the suture exits the seal, through the zigzag pathway of the hub tongue 237 and slide recess 211. Not only does this design positively secure the suture 150 even during patient movements but also minimizes damage to the suture 150 because there is an increased surface retention area, rather than a single point of contact as with some prior art devices.

Catheters that remain in place for extended periods of time must be flushed or cleaned on a regular basis to prevent the buildup of bodily fluids within the catheter. Unlike some prior art devices that contain internal crevices that are difficult to flush, the catheter of the current invention provides a smooth, single pathway for flushing. There are no crevices or other internal cavities within the hub, whereby minimizing the risk of fluid stagnation and the resulting increased risk of infection.

When flushing the catheter, the medical professional connects a syringe or other fluid delivery device to the luer connector 231 of the catheter. A rotational or twisting motion is used to attach and secure the hub to the syringe. Some prior art catheters are susceptible to loosening when disconnected from a syringe because the rotational motion on the hub causes the latching mechanism to become deactivated. The latching hub assembly of the current invention, with its anti-rotation key design, will not loosen or unlatch during axial rotation needed to connect and disconnect of fluid delivery or drainage devices.

The method of removing or repositioning the catheter from the body cavity 5 will now be described with reference to FIGS. 11A, 11B, 11C. FIG. 11A depicts catheter 100 within the body cavity in the latched position prior to removal. To remove catheter 100, the latching mechanism is deactivated by the physician by first sliding the strain relief 270 distally along the catheter shaft 130. This movement exposes the combined hub 230/slide 210 and the slide release tab 213. The physician then manually lifts the tab 213 pulling it away from the center axis of the latching hub assembly 200, as shown by the arrow in FIG. 11B. Moving the tab 213 away from the axis causes the lock catch 215 on the tab 213 to move out of lock recess 241. With the lock catch 215 freed, the slide 210 can be moved distally away from the hub 230, freeing suture 150. With suture 150 no longer under tension, a guidewire 9 can be inserted through hub 230 into the catheter shaft 130 to straighten the distal end of the catheter, as depicted in FIG. 11C. The catheter system can then be removed from the body or can be repositioned within the cavity.

The ease with which the device can be repositioned within the cavity after being latched provides a big advantage over prior art catheters. Using the unlatching method described above, the user easily releases the latching mechanism. Manually unwrapping or untying suture is not required with device and method of the current invention. A separate unlatching key or tool is not necessary as is with some other prior art designs. Once the suture is free, the catheter can be repositioned and the latch reactivated by simply moving the strain relief 270 distally until it snaps in place.

Surfaces which are in intimate contact, and pressed together for some period of time may become partially intermingled and stick together, such as is the case with connector parts. This is especially prevalent when the parts in contact are made of similar materials. When pulled apart the material may be abrased off of one part and attached to the other. This is called "galling". Materials of surfaces of the present invention that are in contact with each other are chosen of dissimilar materials to minimize galling.

Even though the embodiments presented here have been described with tongue 237 located on the hub 230 and slide recess 211 on slide 210, they may easily be reversed such that tongue 237 is now on slide 210 and slide recess 211 is now on hub 230.

Tongue 237 may take many different shapes, positions, and orientations; however, the intention is that it interacts with a corresponding slide recess 211 to secure suture 150.

Similarly, it is envisioned that lock recess 241 on the hub 230 may exchange places with lock catch 215 on slide 210 to function according to the present invention. Accordingly, the recess and catch may also be oriented at different angles to perform the same function.

The invention also envisions that slide slot 243 on hub 230 may exchange places with slide protrusion 217 on slide 210 to perform the same function.

Even though the invention has been described with a single tongue and a single corresponding suture securing recess, it is to be understood that a plurality of these elements may be employed in a device and still be within the scope of the present invention.

The same applies equally to the use of a plurality of a) lock catches and lock recesses, and b) slide protrusions and slide slots.

In other alternative embodiments of the present invention, a cord, wire or line may be used in place of the suture. This would include, but not be limited to braided, twisted, or single filament, natural or synthetic, extruded or formed in other manners.

Also, the slide is described as surrounding and receiving the hub. It would be in the scope of the present invention for the slide to partially surround the hub, or ride on its surface.

The drawings have shown a round cross section, however the invention is not restricted to round or even curved cross sections. The cross sections may be curved, rectangular, a polygonal or any combination of these. The cross sections may also change along the length of the latching hub assembly. It is just required that the slide and hub interact to secure the suture.

While several presently preferred embodiments of the present novel invention have been described in detail herein, many modifications and variations will now become apparent with to those skilled in the art. It is our intent therefore, to be limited only by the scope of the appending claims and not by the specific details presented by way of illustration.

What is claimed is:

1. A catheter device having an anchoring end, comprising:
    a shaft having a proximal portion and a distal portion;
    a hub attached to the proximal portion of the shaft, the hub having a first member, a second member slidably coupled to the first member, and a latch;
    the hub further having:
        a port in a sidewall of the hub and in communication with a lumen of the hub; and
        a deformable sealing material disposed in the port;
        a cord running from the distal portion of the shaft through the shaft and having a free end passing through the deformable sealing material and exiting from the hub; and
        the hub having an unlatched state that allows pulling of the cord such that the distal portion of the shaft forms an anchoring shape, and a latched state in which the latch latches the first and second members together when the second member moves relative to the first member so as to secure the cord to the hub.

2. The catheter device according to claim 1, further comprising a manually operable release member coupled to the latch and being manually operable to release the latch from the latched state, wherein:
    a sliding movement of the second member relative to the first member causes the latch to switch from the unlatched state to the latched state;
    manual operation of the release member together with a reverse sliding movement causing the latch to switch from the latched state to the unlatched state, wherein unlatching of the latch is disabled without first operating the release member.

3. The catheter device according to claim 1, wherein the latch produces a tactile feedback when the first and second members are latched.

4. The catheter device according to claim 1, wherein:
    one of the first and second members has a tongue; and
    the other of the first and second members has a recess that receives the tongue such that when the first and second members are latched, the cord is frictionally secured between the tongue and the recess.

5. The catheter device according to claim 1, wherein the latch comprises:
    a recess disposed on the first member;
    a projection disposed on the second member and adapted to be received in the recess to latch the first and second members together.

6. The catheter device according to claim 5, wherein the hub further comprises a second recess disposed on the first member and adapted to receive the projection disposed on the second member to prevent the second member from sliding off the first member.

7. The catheter device according to claim 5, wherein the latch further comprises a release member coupled to the projection and operable to release the projection from the recess.

8. The catheter device according to claim 7, further comprising a strain relief slidably coupled to the shaft and adapted to cover the release member to limit the ability of a person to release the latch.

9. The catheter device according to claim 5, further comprising a strain relief slidably coupled to the shaft and adapted to cover the projection so as to bias the projection into the recess.

10. The catheter device according to claim 1, further comprising a strain relief slidably coupled to the shaft and adapted to at least partially cover the hub and at least partially cover the proximal portion of the shaft to minimize kinking of the shaft.

11. The catheter device according to claim 1, further comprising:
    an anti-rotation longitudinal slot disposed on one of the first and second members;
    an anti-rotation slide protrusion disposed on the other of the first and second members, and sized to be received in and to move along the anti-rotation longitudinal slot to limit a rotational movement of the second member relative to the first member.

12. The catheter device according to claim 1, further comprising:
a recess disposed on one of the first and second members;
a projection disposed on the other of the first and second members and adapted to be received in the recess to prevent the second member from sliding off the first member.

13. The catheter according to claim 1, wherein
the cord passes through the deformable sealing material disposed in the port.

14. The catheter according to claim 13, wherein the deformable sealing material includes a deformable semi-liquid material.

15. The catheter according to claim 13, wherein the port has an upper enclosure above the deformable sealing material and an opening in the upper enclosure to define an exit for the cord, the upper enclosure having a higher durometer than that of the deformable sealing material.

16. A catheter device having an anchoring end, comprising:
a shaft having a proximal portion and a distal portion;
a hub attached to the proximal portion of the shaft, the hub having a latch;
the hub further having:
a port in a sidewall of the hub and in communication with a lumen of the hub; and
a deformable sealing material disposed in the port;
a cord running from the distal portion of the shaft through the shaft and having a free end passing through the deformable sealing material and exiting from the hub; and
a slide member slidably coupled to the hub, the slide member having an unlatched state that allows pulling of the cord such that the distal portion of the shaft forms an anchoring shape, and a latched state in which the hub and the slide member are latched together by the latch so as to secure the cord to the hub, the latch latching the hub and the slide member when the slide member slidably moves toward the hub.

17. The catheter device according to claim 16, further comprising a manually operable release member coupled to the latch and being manually operable to release the latch from the latched state, wherein:
a sliding movement of the slide member relative to the hub causes the latch to switch from the unlatched state to the latched state;
manual operation of the release member together with a reverse sliding movement causing the latch to switch from the latched state to the unlatched state, wherein unlatching of the latch is disabled without first operating the release member.

18. The catheter device according to claim 16, wherein:
one of the hub and the slide member has a tongue; and
the other of the hub and the slide member has a recess that receives the tongue such that when the first and second members are latched, the cord is frictionally secured between the tongue and the recess.

19. The catheter device according to claim 16, wherein the latch comprises:
a recess disposed on the hub;
a projection disposed on the slide member and adapted to be received in the recess to latch the hub and the slide member together.

20. The catheter device according to claim 18, wherein the hub further comprises a second recess adapted to receive the projection disposed on the slide member to prevent the slide member from sliding off the hub.

21. The catheter device according to claim 16, further comprising:
an anti-rotation longitudinal slot disposed on one of the hub and the slide member;
an anti-rotation slide protrusion disposed on the other of the hub and the slide member, and sized to be received in and to move along the anti-rotation longitudinal slot to limit a rotational movement of the slide member relative to the hub.

22. The catheter device according to claim 16, further comprising:
a recess disposed on one of the hub and the slide member;
a projection disposed on the other of the hub and the slide member and adapted to be received in the recess to prevent the slide member from sliding off the hub.

23. A catheter device having an anchoring end, comprising:
a shaft having a proximal portion and a distal portion;
a hub attached to the proximal portion of the shaft, the hub having a first member, a second member movably coupled to the first member, and a latch;
the hub further having:
a port in a sidewall of the hub and in communication with a lumen of the hub; and
a deformable sealing material disposed in the port;
a cord running from the distal portion of the shaft through the shaft and then through the deformable sealing material;
the latch having an unlatched state in which the cord can be readily pulled such that the distal portion of the shaft forms an anchoring shape;
the latch having a latched state in which the cord is secured to the hub to maintain the anchoring shape of the distal portion;
a manually operable release member coupled to the latch and being manually operable to release the latch from the latched state;
a first predetermined movement of the second member relative to the first member causing the latch to switch from the unlatched state to the latched state;
manual operation of the release member together with a reverse predetermined movement causing the latch to switch from the latched state to the unlatched state.

24. The catheter device according to claim 23, wherein:
one of the first and second members has a tongue; and
the other of the first and second members has a recess that receives the tongue such that when the first and second members are latched, the cord is frictionally secured between the tongue and the recess.

25. The catheter device according to claim 23, wherein the latch comprises:
a recess disposed on the first member;
a projection disposed on the second member and adapted to be received in the recess to latch the first and second members together.

26. The catheter device according to claim 23, further comprising:
an anti-rotation longitudinal slot disposed on one of the first and second members;
an anti-rotation slide protrusion disposed on the other of the first and second members, and sized to be received in and to move along the anti-rotation longitudinal slot to limit a rotational movement of the second member relative to the first member.

27. A method of anchoring and releasing a distal end of a catheter in a body cavity of a patient by a cord, the catheter including a hub having a port in a sidewall of the hub and in communication with a lumen of the hub and a deformable sealing material disposed in the port wherein the cord extends through a lumen of the catheter and then through the deformable sealing material, the method comprising:

latching first and second hub pieces by a predetermined engagement movement between the first and second hub pieces to hold the cord against movement;

unlatching the first hub piece from the second hub piece by a reverse movement of the first and second hub pieces; and manually operating a release member coupled to the hub to enable the step of unlatching, the step of unlatching being disabled without first operating the release member.

28. The method according to claim 27, wherein:

the step of latching is a sliding motion of the first hub piece relative to the second hub piece in a first axial direction of the hub; and the step of unlatching is a sliding motion of the first hub piece relative to the second hub piece in an opposite axial direction from the first axial direction.

29. The method according to claim 28, further comprising:

providing a strain relief that at least partially covers the release member to limit the ability of a person to release the latch; and removing the strain relief to expose the release member prior to the step of manually operating a release member.

\* \* \* \* \*